United States Patent [19]

Pieper

[11] Patent Number: 4,765,326

[45] Date of Patent: Aug. 23, 1988

[54] LOW-FLOW ALARM SYSTEM FOR POWDERED AIR-PURIFYING RESPIRATOR

[75] Inventor: Wendell J. Pieper, Lake Elmo, Minn.

[73] Assignee: Minnesota Mining and Manufacturing Company, St. Paul, Minn.

[21] Appl. No.: 40,342

[22] Filed: Apr. 20, 1987

[51] Int. Cl.[4] .......... A61M 15/00

[52] U.S. Cl. .......... 128/202.22; 128/205.23

[58] Field of Search .......... 128/205.23, 202.22; 116/264, 268; 73/861.65, 861.67; 137/269

[56] References Cited

U.S. PATENT DOCUMENTS

| | | | |
|---|---|---|---|
| 2,408,136 | 9/1946 | Fox | 128/29 |
| 2,914,067 | 11/1959 | Meidenbauer | 128/205.23 X |
| 4,286,589 | 9/1981 | Thompson | 128/205.23 X |
| 4,287,886 | 9/1981 | Thompson | 128/202.22 |
| 4,343,194 | 10/1982 | Dehart et al. | 73/861.65 |
| 4,372,170 | 2/1983 | Dehart et al. | 73/861.61 |
| 4,476,729 | 10/1984 | Stables et al. | 73/861.61 |
| 4,565,092 | 1/1986 | Kompelien | 73/202 |
| 4,570,493 | 2/1986 | Leemhuis | 73/861.62 |

FOREIGN PATENT DOCUMENTS 3032371A 3/1982 Fed. Rep. of Germany .

*Primary Examiner*—Alan Cohan

*Attorney, Agent, or Firm*—Donald M. Sell; Edward T. Okubo

[57] ABSTRACT

A known powered air-purifying respirator has an alarm that is preset to be actuated whenever a Pitot static sensor indicates that the airflow has dropped below a safe level. The invention permits such a respirator to be used with either a tight-fitting facepiece or with a loose-fitting hood or helmet and, without adjusting the preset alarm, can indicate that the airflow has dropped below the proper minimum for whichever is being used. This is accomplished by supplying the respirator with two breathing tubes, a first of which is unobstructed and can be fitted only to a loose-fitting hood or helmet that required high airflow. The other breathing tube can be fitted only to a tight-fitting facepiece and has a protuberance that reduces the cross-sectional area of the chamber in which the Pitot static sensor is mounted so that the alarm is actuated only when the airflow drops below a level that is lower than the alarm-sounding level when the first breathing tube is being used.

18 Claims, 2 Drawing Sheets

LOW-FLOW ALARM SYSTEM FOR POWDERED AIR-PURIFYING RESPIRATOR

BACKGROUND OF THE INVENTION

1. Field of the Invention

The invention provides a system, which can be built into a powered air-purifying respirator for providing an alarm when the flow of air to a hood, helmet, or facepiece drops below a predetermined value. The invention is particularly useful in powered air-purifying respirators such as are used by persons who are being exposed to noxious dust, fumes, mists or chemicals.

2. Description of the Related Art

U.S. Government specifications, as established by NIOSH in 30 CFR 11, require powered air-purifying respirators to supply a minimum airflow of breathable air of 4 cfm (115 liters/min.) for tight-fitting facepieces and 6 cfm (170 liters/min.) for loose-fitting helmets and hoods. To provide reasonable assurance of meeting the necessary specification, powered air-purifying respirators typically are designed to supply substantially higher airflow than required, thus affording a margin of safety against reduced airflow due to battery drain and filter clogging. Such effects are so gradual that the airflow could drop to a dangerously low level without this being noticeable to the user unless the respirator were equipped with a low-flow alarm.

We know of only one powered air-purifying respirator that is available with a low-flow alarm, namely, Model AP-28A of Shigematsu Works Ltd. At the outlet of its blower is a chamber containing a Pitot static sensor which controls a switch that is preset to actuate an alarm whenever the airflow drops below a predetermined level. The preset switch is inaccessibly positioned in the housing of the respirator to guard against accidental or deliberate readjustment of the switch setting. The Shigematsu respirator also has an "economy" setting that activates circuitry controlled by the Pitot static sensor to limit the power from the battery pack to the blower so that no more air is delivered than is necessary.

The alarm of the Shigematsu Model AP-28A is preadjusted to be activated when the airflow drops below 4 cfm (115 liters/minute). If a wearer were to wish to use a loose-fitting hood or helmet in place of a tight-fitting facepiece, the alarm would not be actuated until the airflow had dropped well below the minimum level deemed to be hazardous by NIOSH unless the alarm were preset at the factory for a higher flow rate. If such an adjustment were made, there should be means for distinguishing between the two respirators, such as a different color and/or shape, thus alerting users not to use a respirator with a low-flow alarm setting for a loose-fitting helmet or hood that requires a higher alarm setting.

West German Offenlegungsschrift DE No. 3032371 (laid open Mar. 3, 1982) shows a powered respirator for a loose-fitting hood. At the hood is an L-shaped tube containing a ball that is visible to the wearer's peripheral vision. The ball falls when the airflow drops, thus providing a visual alarm. We are not aware of commercial use of any such visual alarm.

Respirators for hospital patients are commonly equipped with alarms to alert an attendant if the airflow drops below a predetermined minimum. See, for example, U.S. Pat. No. 4,287,886 (Thompson).

3. Other Related Art

U.S. Pat. No. 4,476,729 (Stables et al.) shows a gas or airflow measuring device that employs a Pitot static sensor that is said to indicate more accurately the velocity of gas flowing through a duct by means of a flow nozzle 11 in the duct that reduces the cross-sectional area of the duct from 40 to 60 percent at the impact port of the Pitot static sensor. The Stables patent is cited only because the invention also involves means for reducing the cross-sectional area at the impact port of a Pitot static sensor.

SUMMARY OF THE INVENTION

The invention concerns a powered air-purifying respirator which, like the Shigematsu respirator, has a preset low-flow alarm. Unlike the Shigematsu respirator, the novel respirator can be equipped with a tight-fitting facepiece and/or a loose-fitting hood or helmet, and the alarm indicates that the flow rate has dropped below the proper minimum for whichever is being used.

As in the Shigematsu respirator, the novel low-flow alarm system has a chamber which is formed with an inlet to receive air from a blower and an outlet to deliver air to a breathing tube, and the chamber contains a Pitot static sensor which controls a switch that is preset to actuate an alarm whenever the airflow through said breathing tube drops below a predetermined minimum level. The novel low-flow alarm system differs from that of Shigematsu by comprising:

a second breathing tube including an elongated protuberance which, upon fitting the second tube to the chamber outlet, extends into the chamber to reduce the cross-sectional area of the interior of the chamber at the impact port of the Pitot static sensor so that the alarm is actuated whenever the airflow drops below a second predetermined minimum level that is lower than said first-mentioned predetermined minimum level.

The term "Pitot static sensor" is intended to encompass any device for measuring the velocity of a gas, that is, any device such as a hot-wire anemometer that could be positioned in the aforementioned chamber to sense the velocity of air passing through the chamber, with or without the elongated protuberance being present.

Instead of a protuberance, the invention contemplates any means for effecting a specific reduction in the cross-sectional area of the chamber at the impact port upon attaching a specific breathing tube.

In a prototype powered air-purifying respirator incorporating a low-flow alarm system of the invention, the first-mentioned breathing tube is unobstructed. Normally the alarm-control switch is preset so that when using the first-mentioned breathing tube, the alarm is actuated when the airflow drops below 6 cfm (170 liters/minute), thus permitting its use with a loose-fitting hood or helmet. In designing the protuberance of the second breathing tube for use with a tight-fitting facepiece, the requisite percentage reduction in cross-sectional area provided by the protuberance was empirically determined so that the alarm-controlling switch (at its original setting) would not actuate the alarm until the flow rate fell to 4 cfm (115 liters/minute).

In order to use the novel respirator with a helmet or hood designed to have only minimal leakage, it may be desirable to provide a third breathing tube, the protuberance of which at the impact port of the Pitot static sensor would be substantially smaller than that of the second breathing tube. This would cause the switch to actuate the alarm at a predetermined airflow level intermediate specifications for loose-fitting hoods and helmets and for tight-fitting facepieces.

In the aforementioned prototype respirator, the chamber has a substantially cylindrical collar and a cuff at the inlet of each of the breathing tubes that fits over the collar, and the protuberance is permanently affixed to the cuff of the second breathing tube. At the outlet of the first-mentioned breathing tube is a first fitting adapted for attachment to a loose-fitting hood or helmet, and at the outlet of the second breathing tube is a second fitting that is incompatible with the first fitting and uniquely adapted for attachment to a tight-fitting facepiece. Because the first and second fittings are incompatible, it is impossible to make an accidental error by using with a loose-fitting hood or helmet a breathing tube that is intended for use only with a tight-fitting facepiece.

Further disclosure of the low-flow alarm system of the invention is included in the description of the drawing.

THE DRAWING

In the drawing,

FIG. 1 is a fragmentary schematic section through the aforementioned prototype respirator incorporating a low-flow alarm system of the invention; and FIG. 2 is an enlarged cross-sectional view along line 2—2 of FIG. 1; and FIG. 3 in a perspective view of the insert of the respirator of FIGS. 1 and 2.

DETAILED DESCRIPTION

Figure 1:
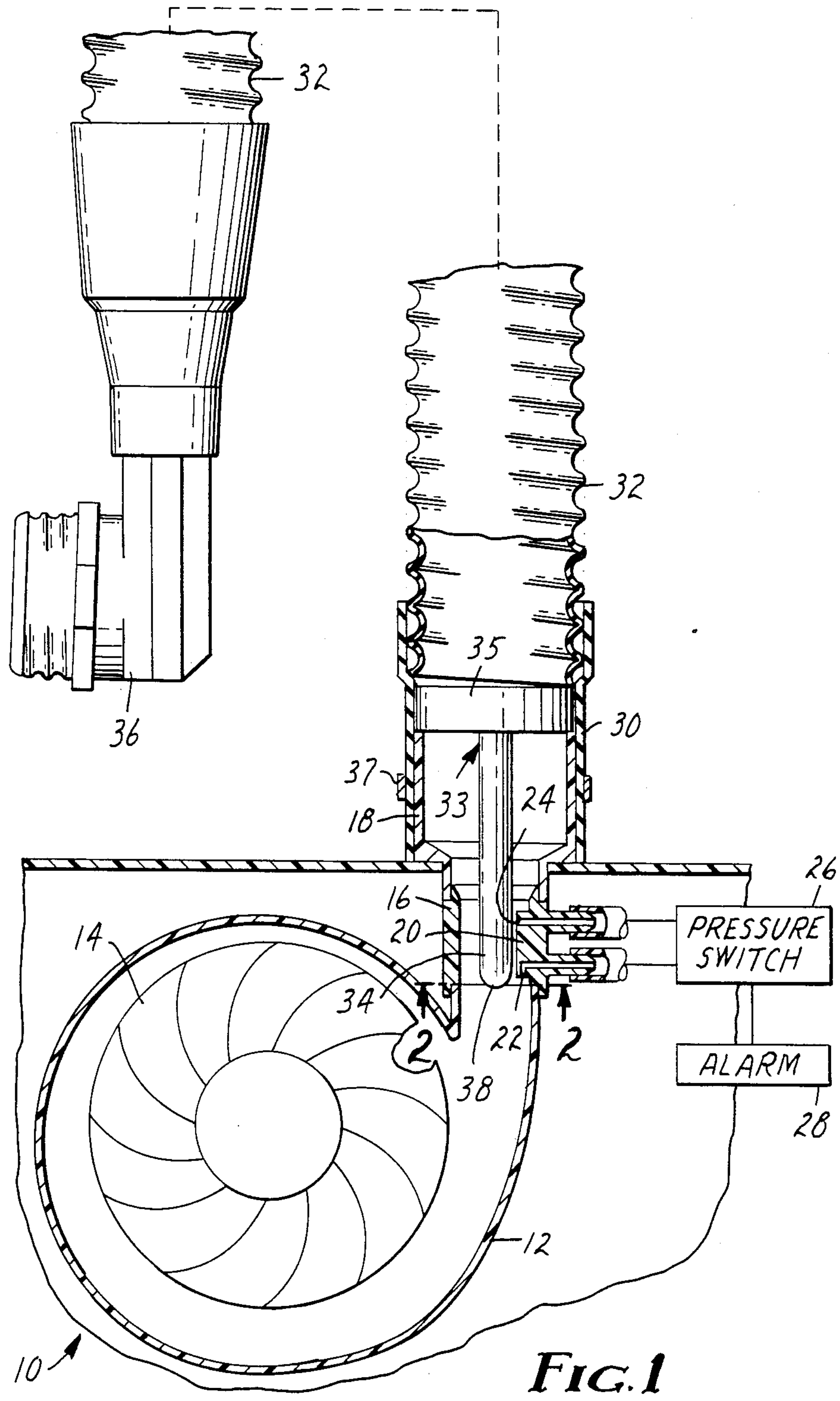

The illustrated powered air-purifying respirator 10 has a housing 12 containing a centrifugal blower 14 and a chamber 16 at the exit of the blower. At the outlet from the chamber is a cylindrical collar 18. Mounted in the chamber 16 is a Pitot static sensor 20 that has an impact port 22 directly facing the flow of air and a static port 24. The Pitot static sensor is pneumatically connected to a switch 26 that is preset, in a manner well known in the art, to actuate an audible alarm 28 whenever the airflow drops below a predetermined level.

The respirator 10 is intended for use with two breathing tubes which are identical to each other except in two respects. The inlet of the first breathing tube (not illustrated) has a cuff like the cuff 30 of the second breathing tube 32 that is illustrated in the drawing, but the first breathing tube is unobstructed. In contrast, the second breathing tube 32 contains an insert 33 consisting of an elongated, cylindrical protuberance 34 and a spoked base 35 which is adhesively bonded to the inner face of its cuff 30. The cuff is formed of a deformable plastic, and a clamp 37 is positioned over the cuff to compress the cuff against the collar 18.

The second difference between the first and second breathing tubes is that at the outlet of the first breathing tube is a first fitting that is identical to the cuff 30 and fits a collar on a loose-fitting helmet or hood (not shown). At the outlet of the second breathing tube 32 is a second fitting 36 which is uniquely adapted to fit a tight-fitting facepiece (not shown). Because the second fitting 36 is incompatible with the first fitting, it would not be possible to connect either breathing tube except to a facepiece, hood or helmet for which it is designed. Hence, a single respirator may be equipped with both breathing tubes, one to be used with a tight-fitting facepiece and the other with a loose-fitting helmet or hood. The absence of the protuberance in the first breathing tube and its presence in the second ensures that the alarm will sound at the appropriate airflow level for each use. This is accomplished automatically without changing the setting of the preset alarm-controlling switch 26.

The first breathing tube is intended for use with a loose-fitting hood or helmet (not shown) requiring relatively high airflow, e.g., at least the 6 cfm (170 liters/-min.) of the above cited specification. While the cuff of the first breathing tube is clamped to the collar 18, the alarm-controlling switch 26 is preset so that the alarm 28 is actuated whenever the airflow drops below 6 cfm (170 liters/min.).

When the cuff 30 of the second breathing tube 32 is clamped to the collar 18, the protuberance 34 extends upstream of the impact port 22 of the Pitot static sensor 20, thus reducing the cross-sectional area of the interior of the chamber 16 at the impact port. The required percentage reduction in cross-sectional area is determined empirically so that the alarm-controlling switch 26 actuates the alarm when the flow rate drops below 4 cfm (115 liters/min.) while the second breathing tube 32 is attached.

As illustrated in FIG. 1, the Pitot static sensor is preferably positioned to one side of the interior of the chamber 16 for two reasons. First, it causes less obstruction to airflow than if it were more centrally positioned. Second, this permits the protuberance 34 to be mounted centrally as illustrated and thus more easily inserted into the chamber 16. The protuberance 34 is rounded at 38 to avoid a sharp edge that otherwise might cause damage upon being inserted into or removed from the chamber.

EXAMPLE

Figure 3:
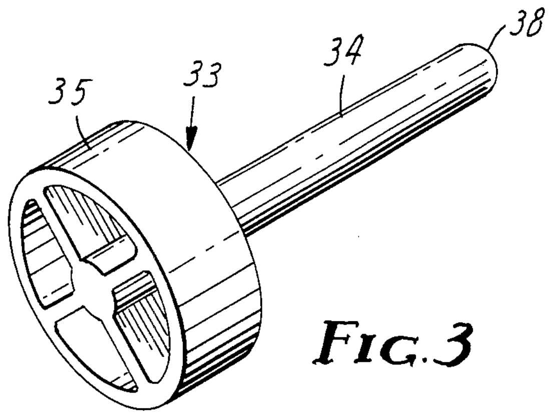
Figure 2:
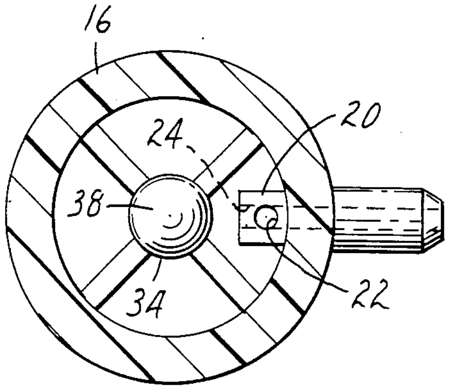

The aforementioned prototype was constructed using a centrifugal blower and battery powered 4.8-volt D.C. motor having a nominal 8000 rpm in an ABS housing. The housing was fitted with a filter unit to purify the intake air and an outlet to deliver the filtered air. A chamber, which had a Pitot static sensor mounted on its inner wall, was adhesively attached to the housing at the exit of the blower. A first breathing tube was assembled from flexible corrugated tubing and fitted with two identical cuffs made of plasticized PVC which were adhesively bonded to the tubing. The Pitot static sensor was pneumatically connected to a pressure switch which was factory adjusted to trigger an audible alarm at an airflow below 6 cfm (170 liters/min.) with the first breathing tube in place. A second breathing tube was constructed from the same corrugated tubing to have at its inlet a cuff identical to the cuffs of the first breathing tube and to have at its outlet a fitting uniquely adapted to fit a tight-fitting face mask. Adhesively bonded to the cuff of the second breathing tube was an insert as illustrated in FIG. 3.

Significant dimensions were:

| | |
|---|---|
| I.D. of chamber 16 at impact port 22 | 1.93 cm |
| Pitot static sensor 20 | |
| height along diameter | 0.41 cm |
| width along circumference | 0.43 cm |
| Protuberance 34 | |
| length | 5.72 cm |
| diameter | 0.76 cm |
| Approximate reduction in | 15% |

-continued

| | |
|---|---|
| cross-sectional area | |
| I.D. of cuff 36 | 3.18 cm |

When the prototype was used with the first breathing tube and a loose-fitting helmet, the alarm reliably sounded whenever the airflow dropped below 6 cfm (170 liters/minute) as measured by an airflow meter, including tests allowing the battery to run down and tests in which the airflow decreased due to a clogged filter or other blockage of the breathing tube.

When the first breathing tube was replaced by the second breathing tube connected to a tight-fitting facepiece, the alarm sounded whenever the airflow dropped below 4 cfm (115 liters/minute).

Among changes that could be made in the prototype respirator is that the first breathing tube could be integral with or permanently attached to a loose-fitting helmet or hood, and the second breathing tube could likewise be integral with or permanently attached to a tight-fitting facepiece.

I claim:

1. Low-flow alarm system for a powered air-purifying respirator comprising a chamber which is formed with an inlet to receive air from a blower and an outlet to deliver air to a breathing tube, the chamber containing a Pitot static sensor which controls a switch that is preset to actuate an alarm whenever the airflow through said breathing tube drops below a predetermined level, wherein the improvement comprises:
 means for reducing the cross-sectional area of the interior of the chamber at the impact port of the Pitot static sensor so that the alarm is actuated whenever the airflow drops below a second predetermined level that is lower than said first-mentioned predetermined level.

2. Low-flow alarm system for a powered air-purifying respirator comprising a chamber which is formed with an inlet to receive air from a blower and an outlet to deliver air to a breathing tube, the chamber containing a Pitot static sensor which controls a switch that is preset to actuate an alarm whenever the airflow through said breathing tube drops below a predetermined level, wherein the improvement comprises:
 a second breathing tube including an elongated protuberance which, upon fitting the second tube to the chamber outlet, extends into the chamber to reduce the cross-sectional area of the interior of the chamber at the impact port of the Pitot static sensor so that the alarm is actuated whenever the airflow drops below a second predetermined level that is lower than said first-mentioned predetermined level.

3. Low-flow alarm system as defined in claim 2 wherein the outlet of the first-mentioned breathing tube has a first fitting adapted for attachment to a loose-fitting hood or helmet, and the outlet of the second breathing tube has a second fitting that is incompatible with the first fitting and adapted for attachment to a tight-fitting facepiece.

4. Low-flow alarm system as defined in claim 3 wherein the chamber outlet has a substantially cylindrical collar, and the inlet of each of the breathing tubes has a cuff that fits over said collar.

5. Low-flow alarm system as defined in claim 4 wherein the cuff of each of the breathing tubes is a deformable plastic, and a clamp is positioned over the cuff to compress the cuff against the collar.

6. Low-flow alarm system as defined in claim 2 wherein the protuberance is permanently affixed to the cuff, is substantially cylindrical, and is elongated along its cylindrical axis.

7. Low-flow alarm system as defined in claim 6 wherein the protuberance is part of insert having a spoked base which is adhesively bonded to the inner face of the cuff.

8. Low-flow alarm system as defined in claim 6 wherein the extremity of the protuberance is rounded.

9. Low-flow alarm system as defined in claim 6 wherein the protuberance is elongated substantially along the axis of the cuff.

10. Low-flow alarm system as defined in claim 2 wherein the interior of the first-mentioned breathing tube is substantially unobstructed.

11. Low-flow alarm system as defined in claim 10 wherein the switch is preset so that the alarm is actuated at a first predetermined minimum level of about 170 liters/minute when the cuff of the first breathing tube is fitted to the outlet of the chamber, and the size of said protuberance at the impact opening of the Pitot static sensor is selected so that the alarm-adjusting means actuates the alarm at a second predetermined minimum level of about 115 liters/minute when the cuff of the second breathing tube is fitted to the outlet.

12. Low-flow alarm system as defined in claim 2 and including a third breathing tube equipped with a protuberance, the area of which at the impact opening of the Pitot static sensor is substantially different from that of the protuberance of the second breathing tube.

13. Low-flow alarm system for a positive-pressure respirator comprising
 a chamber which is formed with an inlet to receive air from a blower and an outlet to deliver air to a breathing tube,
 a Pitot static sensor mounted in the interior of the chamber,
 an alarm,
 a first breathing tube which is unobstructed and adapted to fit tightly with the chamber outlet,
 a switch that is preset to actuate the alarm whenever the airflow from the chamber outlet to the first breathing tube drops below a predetermined level,
 a second breathing tube including an elongated protuberance which, upon fitting the second tube to the chamber outlet, extends into the chamber to reduce the cross-sectional area of the interior of the chamber at the impact port of the Pitot static sensor so that the alarm is actuated whenever the airflow drops below a second predetermined level that is lower than said first-mentioned predetermined level.

14. Low-flow alarm system as defined in claim 13 wherein the chamber outlet has a substantially cylindrical collar, and the inlet of each of the breathing tubes has a cuff which fits tightly over the collar.

15. Low-flow alarm system as defined in claim 14 wherein the outlet of the first breathing tube has a first fitting adapted for attachment to a loose-fitting hood or helmet, and the outlet of the second breathing tube has a second fitting that is incompatible with the first fitting and adapted for attachment to a tight-fitting facepiece.

16. A powered air-purifying respirator for supplying air to helmets, hoods and facepieces and comprising a housing containing a blower, a chamber at the exit of the blower, and an outlet from the chamber, a Pitot static sensor mounted in the interior of the chamber, first and second breathing tubes, a first end of each of which is adapted to fit tightly with said chamber outlet, an alarm, a switch that is controlled by the Pitot static sensor and is preset to actuate the alarm whenever the airflow from the chamber outlet to the first breathing tube drops below a predetermined level, a second breathing tube including an elongated protuberance which, upon fitting the second tube to the chamber outlet, extends into the chamber to reduce the cross-sectional area of the interior of the chamber at the impact port of the Pitot static sensor so that the alarm is actuated whenever the airflow drops below a second predetermined level that is lower than said first-mentioned predetermined level.

17. A powered air-purifying respirator as defined in claim 16 wherein the first breathing tube is unobstructed.

18. A powered air-purifying respirator as defined in claim 17 wherein the outlet of the first breathing tube has a first fitting adapted for attachment to a loose-fitting hood or helmet, and the outlet of the second breathing tube has a second fitting that is incompatible with the first fitting and adapted for attachment to a tight-fitting facepiece.

* * * * *